US010168272B2

(12) United States Patent
Malissek et al.

(10) Patent No.: US 10,168,272 B2
(45) Date of Patent: Jan. 1, 2019

(54) SAMPLING APPARATUS COMPRISING A REFERENCE MARKER

(71) Applicant: Gerresheimer Regensburg GmbH, Regensburg (DE)

(72) Inventors: Juergen Malissek, Schwandorf (DE); Andre Nadrowski, Buende (DE)

(73) Assignee: Gerresheimer Regensburg GMBH, Regensburg (DE)

( * ) Notice: Subject to any disclaimer, the term of this patent is extended or adjusted under 35 U.S.C. 154(b) by 100 days.

(21) Appl. No.: 15/238,630

(22) Filed: Aug. 16, 2016

(65) Prior Publication Data
US 2017/0052110 A1    Feb. 23, 2017

(30) Foreign Application Priority Data

Aug. 17, 2015 (DE) .................. 10 2015 113 557

(51) Int. Cl.
| | |
|---|---|
| *G01N 21/03* | (2006.01) |
| *G01B 11/14* | (2006.01) |
| *G01N 33/493* | (2006.01) |
| *G01N 15/14* | (2006.01) |
| *B41M 5/24* | (2006.01) |

(Continued)

(52) U.S. Cl.
CPC ............ *G01N 21/03* (2013.01); *B41M 5/24* (2013.01); *G01B 11/14* (2013.01); *G01N 15/1463* (2013.01); *G01N 33/493* (2013.01); *G01N 2015/0053* (2013.01); *G01N 2015/0065* (2013.01); *G01N 2015/0693* (2013.01)

(58) Field of Classification Search
CPC .... G01N 21/03–21/09; G01N 15/1463; G01N 33/493; G01N 2015/0693; G01N 2015/0053; G01N 2015/0065; G01B 11/14; B41M 5/24

USPC ................................................. 356/246, 440
See application file for complete search history.

(56) References Cited

U.S. PATENT DOCUMENTS

| | | | |
|---|---|---|---|
| 3,663,155 A | 5/1972 | Gray et al. | |
| 2010/0025387 A1 | 2/2010 | Arai et al. | |
| 2016/0334612 A1* | 11/2016 | Stoecker | .................. B01L 3/54 |

FOREIGN PATENT DOCUMENTS

| | | |
|---|---|---|
| DE | 10118156 | 10/2001 |
| DE | 10137864 | 2/2003 |

(Continued)

OTHER PUBLICATIONS

German Examination Report, dated Aug. 18, 2017, in German Patent Application No. 10 2015 113557.4, a related application, 3 pp.

(Continued)

*Primary Examiner* — Hina F Ayub
*Assistant Examiner* — Amanda Merlino
(74) *Attorney, Agent, or Firm* — Leydig, Voit & Mayer, Ltd.

(57) ABSTRACT

Sampling apparatus made of a material such as plastic material and/or glass, a body of the material forming a cavity for receiving a liquid sample, the sampling apparatus comprising a gauging region which can be arranged in a focus region of a visual measuring device for determining the position of the sampling apparatus and/or of the cavity, and in which at least one reference marker is arranged which can be detected by means of the visual measuring device, wherein the reference marker is formed in an inner region of the body that is remote from the surface.

18 Claims, 4 Drawing Sheets

(51) Int. Cl.
*G01N 15/00* (2006.01)
*G01N 15/06* (2006.01)

(56) References Cited

FOREIGN PATENT DOCUMENTS

| | | |
|---|---|---|
| DE | 10 2005 036529 | 2/2007 |
| EP | 2896458 | 7/2015 |
| WO | 2012/025220 | 3/2012 |

OTHER PUBLICATIONS

German Examination Report, dated Apr. 21, 2016, corresponding to German Application No. 10 2015 113 557.4 (filed Aug. 17, 2015), parent of the present application, 3 pp.

* cited by examiner

SAMPLING APPARATUS COMPRISING A REFERENCE MARKER

CROSS-REFERENCE TO RELATED APPLICATIONS

This patent application claims the benefit of priority from German application 10 2015 113 557.4, filed on Aug. 17, 2015, the contents of which are incorporated herein by reference.

BACKGROUND OF THE INVENTION

The invention relates to a sampling apparatus made of a material such as plastic material and/or glass, a body of the material forming a cavity for receiving a liquid sample, the sampling apparatus comprising a gauging region which can be arranged in a focus region of a visual measuring device for determining the position of the sampling apparatus and/or of the cavity, and in which at least one reference marker is arranged which can be detected by means of the visual measuring device.

Disposable products (also known as "consumable devices") used in medical diagnostics are known from the prior art. For example, disposable products exist for urine analysis which are used as sampling apparatuses for carrying out a fluid image analysis. After filling a region of the disposable product intended for this purpose with the urine sample, said product is placed into a suitable measuring device. Examination images can then be taken and stored. After segmenting and classifying particles contained in the urine, it is usually possible to draw a conclusion on potential illnesses.

Using the fluid image analysis, bacteria in the µm size range can be gauged, for example. Furthermore, it is also possible to identify blood components or salts, for example.

Generally, in systems for visually measuring or analysing certain regions of selected materials (e.g. plastic material or glass), which optionally contain certain particles, elements or other substances to be identified owing to the addition or removal of particular liquids, solutions or additives, the regions intended therefor need to be marked or indicated in or on the material. The process step of measuring or analysing the specified region then takes place largely automatically by means of a visual measurement/evaluation system.

In order for it to be possible for the measuring device to determine and adjust the system focus as reliably as possible, visual reference markers are arranged in the measuring region of the sampling apparatus, which markers can be detected by means of the measuring device and represent the regions in which focus is intended to be measured. For example, these reference markers are in the form of conical markers or reference marks in the material of the sampling apparatus for the quality assurance of the function. These reference markers make it possible to reliably determine the system focus and at the same time provide a direct feedback mechanism for the electrical adjustable focus system.

Placing reference features for the measuring region to be examined by means of the visual measuring system often presents a problem, since the markers in the material vary in shape, size and visual appearance, and may extend into the nano range depending on the application. It is known from the prior art to produce said reference markers by means of a standard laser process, which acts on the surface of the material of the sampling apparatus, for example by means of direct laser marking.

The drawback here, however, is that by applying the reference markers by means of laser marking, which acts on the object surface or on the object surface and in the region close to the surface, particles are deposited on the surface or on the object surface and in the region close to the surface. Said particles settle on the sampling apparatus and/or in the cavity and may thus negatively affect the measurements made by the measuring device in the region of the markers (reference markers). The particles accumulated during laser marking on the object surface are incorporated into the visual evaluation carried out by the measuring system and thus distort the measurement results.

Making markers in general in a workpiece is known from the prior art. Furthermore, the prior art discloses laser markers for applying a matrix code to an object and read-out equipment for reading out the matrix code applied by laser marking.

However, the prior art does not disclose how a measurement that is less susceptible to faults can be implemented in a sampling apparatus.

SUMMARY OF THE INVENTION

The problem addressed by the invention is therefore to provide sampling apparatuses for use in fluid image analysis of which the reference markers can be detected more precisely. Furthermore, a method for making said markers (reference markers, reference marks) is also intended to be disclosed.

The problem addressed by the invention is solved by a sampling apparatus made of a material such as plastic material and/or glass, a body of the material forming a cavity for receiving a liquid sample, the sampling apparatus comprising a gauging region which can be arranged in a focus region of a visual measuring device for determining the position of the sampling apparatus and/or of the cavity, and in which at least one reference marker is arranged which can be detected by means of the visual measuring device, wherein the reference marker is formed in an inner region of the body that is remote from the surface.

The reference marker is particularly preferably only arranged in the inner region remote from the surface. This means that a method which makes the marker on the surface or on the surface and at the same time also in an inner region remote from the surface (for example stamping) is not used. Within the meaning of the invention, the body of the material is understood to mean that a body is formed by means of the material. This may have a particular shape and for example may be designed to surround the cavity. The body and the cavity are parts of the sampling apparatus in this case.

By making the reference marker inside the material, said marker can be produced so as to be free of particles in the viewing region. Several possible methods are conceivable here for making the marker. For example, a chip or an insert can be injected into the sampling apparatus. Furthermore, it is possible to detect the reference marker by detecting the change in the refractive index at a transitional surface between two different materials. Reference markers and liquid samples (urine) are thus not in one plane when viewed from the measuring device. The position of the reference markers can thus be determined more precisely, since any solids in urine do not prevent said markers from being visually detected.

In addition to these possibilities, it has proven to be particularly advantageous, in terms of the cost and simplicity of the production method for sampling apparatuses of this type, for the reference marker to be a conversion product of the material, and preferably only one conversion product of the material. This means that the reference marker, which can also be referred to as a product, for example, is only produced by converting the starting material (plastic material/glass), which can be referred to as a reactant, for example, without introducing an additional material, and therefore without introducing an external reaction partner.

It is particularly advantageous for the reference marker to be the product of laser inner engraving in the material, and therefore the reference marker is formed by means of laser inner engraving. In the process, by accordingly focussing the laser beam, a marker is made inside the material, that is to say below and remote from the surface of the material. The process can also accordingly be referred to as a sub-surface process. The reference markers are preferably imaged in the material and at any depth in the material as a hologram so as to be free of particles. Therefore, it can be ensured that the sampling apparatus is delivered so as to be free of particles, since the sub-surface process does not leave any residues on the sampling apparatus and particles do not form on the object surface to be processed that in turn may settle on the surface of the sampling apparatus. As a result, more precise measurement using the measuring device is possible. Sampling apparatuses of this type are not known from the prior art.

Laser inner engraving is a method for depicting images of three-dimensional bodies within a transparent solid body. In addition to glass, other materials such as sapphire, diamond, PMMA and polycarbonate can be inner-engraved. In this process, three-dimensional images can be produced within the solid body. Using special software, a point cloud is first calculated, which represents the shape of the subsequent image. The following is applicable: the points are densest at the lightest points in the starting image, and the darkest regions only have a few points.

In order to produce an image point, a laser beam (or beam cluster) is deflected on the X and Y axes using two mirrors, operated by galvanometers, by means of a scanner, and is focused into the interior of the body using a lens. At the point of focus, the spatial and temporal energy density of the pulsed laser beam is so high that the glass is thermally distorted (by cracking, melting and evaporating) by ionisation and plasma formation, while the still wide beam in front and behind does not damage either the two glass surfaces or the focussing lens. The resulting small points, which are a few micrometers (μm) in size, are visible in daylight as white points due to light refraction and scattering.

Three mechanical movement axes, with either the object or the laser head being moved together with the scanner, make it possible to arrange the points at any coordinates within the block of material. By providing many points, two-dimensional or three-dimensional markers are produced in the material.

The smaller the wavelength of the laser, the smaller the possible image points that can be produced. Therefore, the resolution and the precision of the resulting image (reference markers) are increased.

It would also be conceivable to produce the sampling apparatus by means of injection moulding, the reference markers being provided in the form of inserts around which injection moulding is to take place, and being placed into the injection-moulding cavity. However, unlike laser inner engraving, high pressures arise in this process, which constitute a high mechanical load and could possibly even result in the reference markers being displaced. Furthermore, the method is time-consuming owing to the large number of reference markers that are required.

For the sampling apparatus according to the invention, it is advantageous for the reference markers to be essentially in the form of a generated surface and a top surface of a truncated cone. A truncated cone is understood to mean a rotational body that results when a smaller cone is cut from a straight-sided circular cone in parallel with the bottom surface. The larger of the two resulting parallel circular surfaces is the bottom surface, and the smaller of the two is the top surface. The third of the bordering surfaces is referred to as the generated surface, with two surface lines of the generated surface being visible in a cross-sectional view of a truncated cone in each case. The height of the truncated cone is understood to mean the distance between the bottom surface and top surface. In other words, the preferred shape of the reference markers forms the shell of a truncated cone without the shell belonging to the bottom surface.

The rotationally symmetrical shape is advantageous because it is thus in principle sufficient to arrange the longitudinal axis of the sampling apparatus correctly relative to the measuring device. If the position of the sampling apparatus differs because of a rotation in a plane parallel to the longitudinal axis, the visual measuring device could still detect the reference marker at the same angle.

In addition, this shape is advantageous if the position of the visual measuring device relative to the reference markers is selected such that the light beams are precisely parallel to the surface line. In other words, the angle forming the generated surface relative to the bottom surface is dependent on the selected relative position. Therefore, the best possible coverage of the light beams and thus the best detection is possible. Therefore, in projection, the bottom surface and the generated surface form a dark outer ring and a slightly lighter inner ring.

Furthermore, in practice it has proven advantageous for an angle between a surface line of the truncated cone and a longitudinal axis of the truncated cone to have a value within a range of 5-20°, preferably of 10°.

It has likewise proven advantageous for a diameter of the top surface to have a value within a range of 1-5 μm, preferably of 3.2 μm and/or a diameter of a bottom surface of the truncated cone that is parallel to the top surface to have a value within a range of 1-10 μm, preferably of 5 μm.

For the present use in fluid image analysis, it is also preferable for the reference markers to be arranged relative to one another at a distance of 100-1000 μm, preferably 200-500 μm, more preferably approximately 250 μm.

It is likewise advantageous for one to ten, preferably three, rows of reference markers to be arranged along a longitudinal axis of the sampling apparatus and one to ten, preferably three, rows of reference markers to be arranged along a width axis of the sampling apparatus.

In practice, it has also proven worthwhile for the material of the sampling apparatus to be PMMA (polymethyl methacrylate).

The problem addressed by the present invention is also solved by a method for making at least one reference marker in a sampling apparatus made of a material such as plastic material and/or glass, a body of the material forming a cavity for receiving a liquid sample, and the sampling apparatus comprising a gauging region to be arranged in a focus region of a visual measuring device, wherein the reference marker, which can be detected by means of the visual measuring device, is made in an inner region of the body that is remote from the surface, within the gauging region, by means of laser inner engraving.

Further advantages, aims and properties of the present invention are explained on the basis of the following description of the accompanying drawings. Like components may have the same reference signs in the different embodiments.

DETAILED DESCRIPTION OF THE INVENTION

Figure 1:
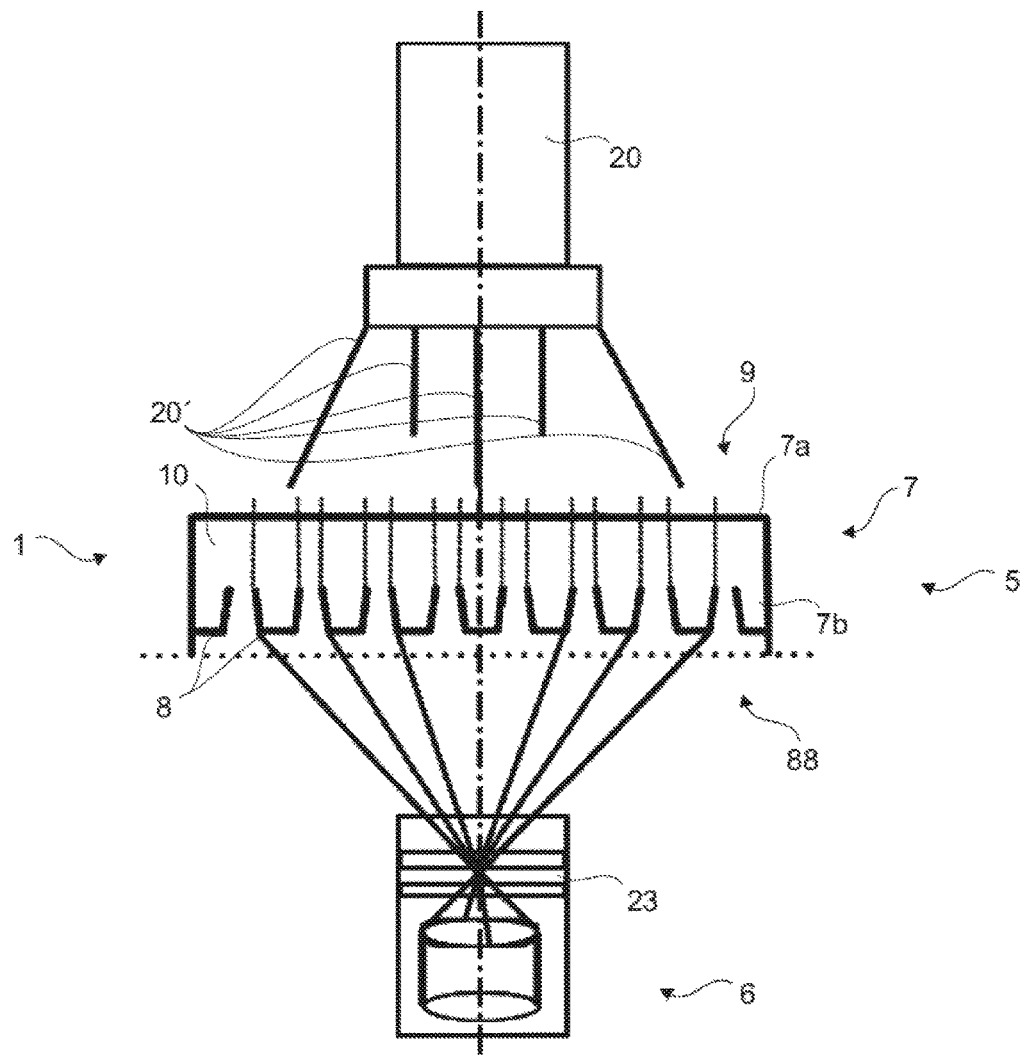
FIG. 1 is a schematic view of the principle of visually detecting the reference markers.

FIG. 1 shows the principle of fluid image analysis, a highly simplified sampling apparatus 1 made of PMMA being arranged in a focus region 5 of a visual measuring device 6 (a camera in this example) comprising a lens 23. In order to assist the measuring device 6, a light source 20 is provided which emits light beams 20'. The sampling apparatus 1 comprises a row 88 of integrated reference markers 8 (of which two are labelled with reference signs by way of example) in a region 7b of a material region 7 that is remote from the surface, but has no reference markers in a region 7a that is close to surface. In the present case, the reference marker 8 is exclusively a conversion product of the material 9 of the sampling apparatus 1 itself, and is made in particular by means of laser inner engraving.

The measuring device 6 can then detect the reference markers 8 and accordingly identify the position of the sampling apparatus 1 relative to the measuring device 6, for example. The recorded images can thus be clearly assigned to this position and can be accordingly evaluated.

FIG. 2 shows, again in a highly simplified manner and with shading, the relevant measuring region 4 or gauging region 4 of a sampling apparatus 1, which region is arranged, for the analysis (FIG. 1), in the focus region 5 of the visual measuring device 6 for determining the position of the sampling apparatus 1 and/or of a cavity 2, and in which region the at least one reference marker 8 (see FIG. 1), which can be detected by means of the visual measuring device 6, is made in the material 9. Likewise, the cavity 2 for receiving a liquid sample 3 is shown, with the cavity 2 being formed by a body 10 of the material 9, and the liquid sample 3 is represented by dots in only a small region of the cavity 2.

The sampling apparatus 1 provides a zone in which some of the elements of the liquid sample 3 can fall towards the bottom of the sampling apparatus 1, while some other elements remain in the fluid provided. The elements that have fallen to the bottom then move in a region of the camera that is clearly visible below the focus plane, while the elements to be measured are still in the focus region of the measuring device.

The shown coordinate system containing the axes x, y, z, and the longitudinal axis 1a and the width axis 1b of the sampling apparatus 1, illustrates the perspective of the present view.

Figure 2:
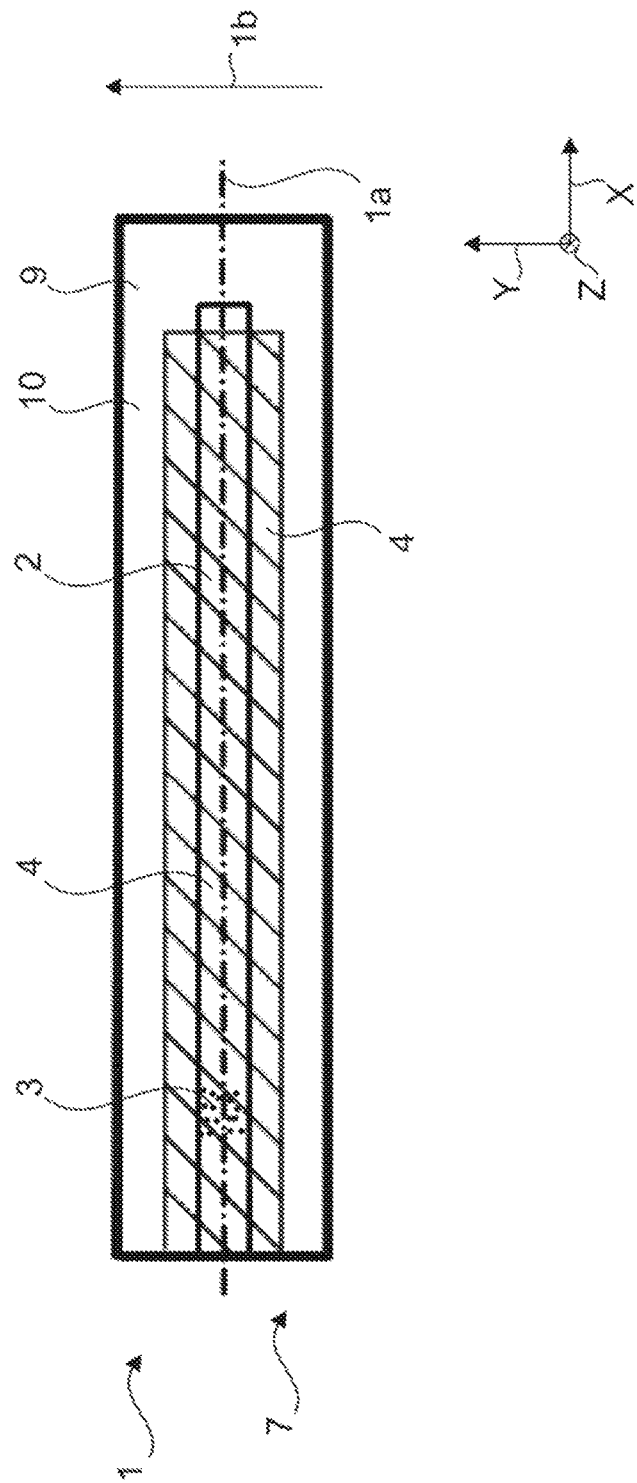
FIG. 2 is a highly simplified view of a sampling apparatus comprising a measuring region.
Figure 3:
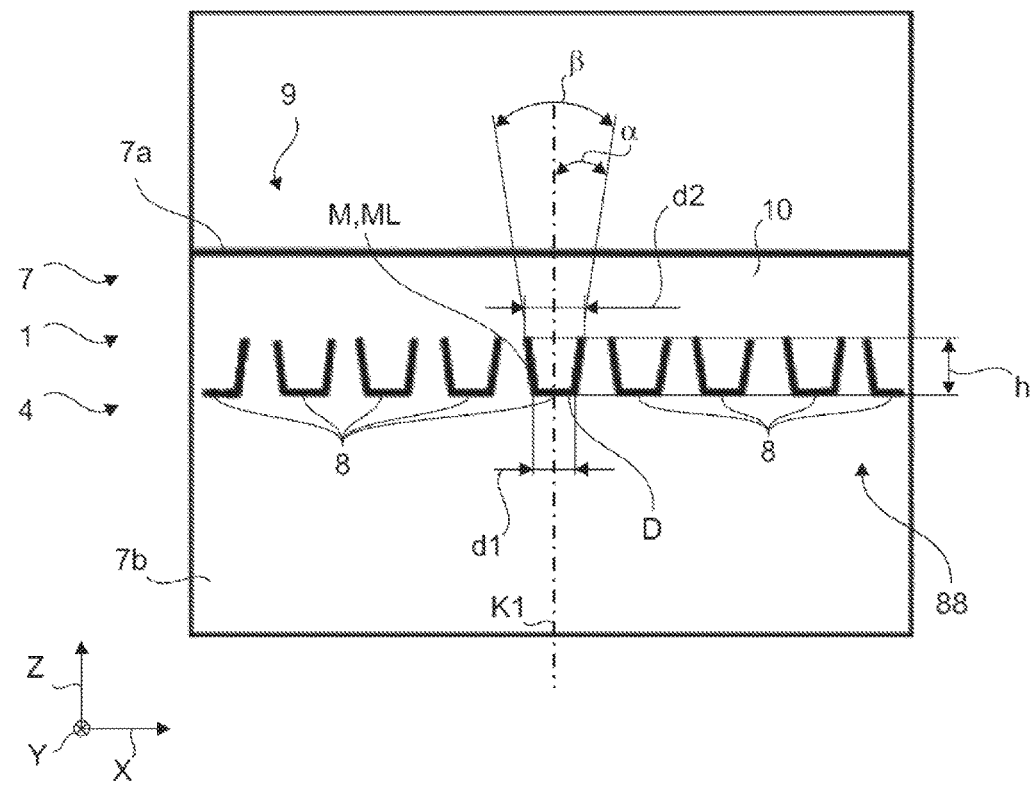
FIG. 3 shows the arrangement of reference markers in the measuring region of the sampling apparatus according to FIG. 2.

FIG. 3 shows the arrangement of reference markers 8 in the measuring region 4 of the sampling apparatus 1 according to FIG. 2, in accordance with a detail of a cross section along the longitudinal axis 1a of the sampling apparatus 1, the reference markers 8 essentially being in the form of a generated surface M and a top surface D of a truncated cone. Furthermore, an angle $\beta$ between two surface lines ML, which are in a plane containing a longitudinal axis K1 of the truncated cone, has a value of 20° in the present case. The value of this angle $\beta$ corresponds to twice the value of the angle $\alpha$ between one of the surface lines ML and the longitudinal axis K1.

This figure clearly shows a plurality of reference markers 8 in the material 9, which have been made in a row 88 by laser inner engraving and represent visual information in the material 9. For example, the sampling apparatus 1 comprises, in at least one plane viewed in parallel with its longitudinal axis 1a, a row 88 of from 10 to 200, preferably 100, reference markers 8 arranged beside one another. It is conceivable that, when viewed in the width direction y, at least three rows 88 of this type are arranged at a distance of 250 μm.

In the present case, the remaining dimensions d1, d2, h of the reference marker 8 are as follows: d1=3.2 μm, d2=5 μm, h=5 μm.

Figure 4:
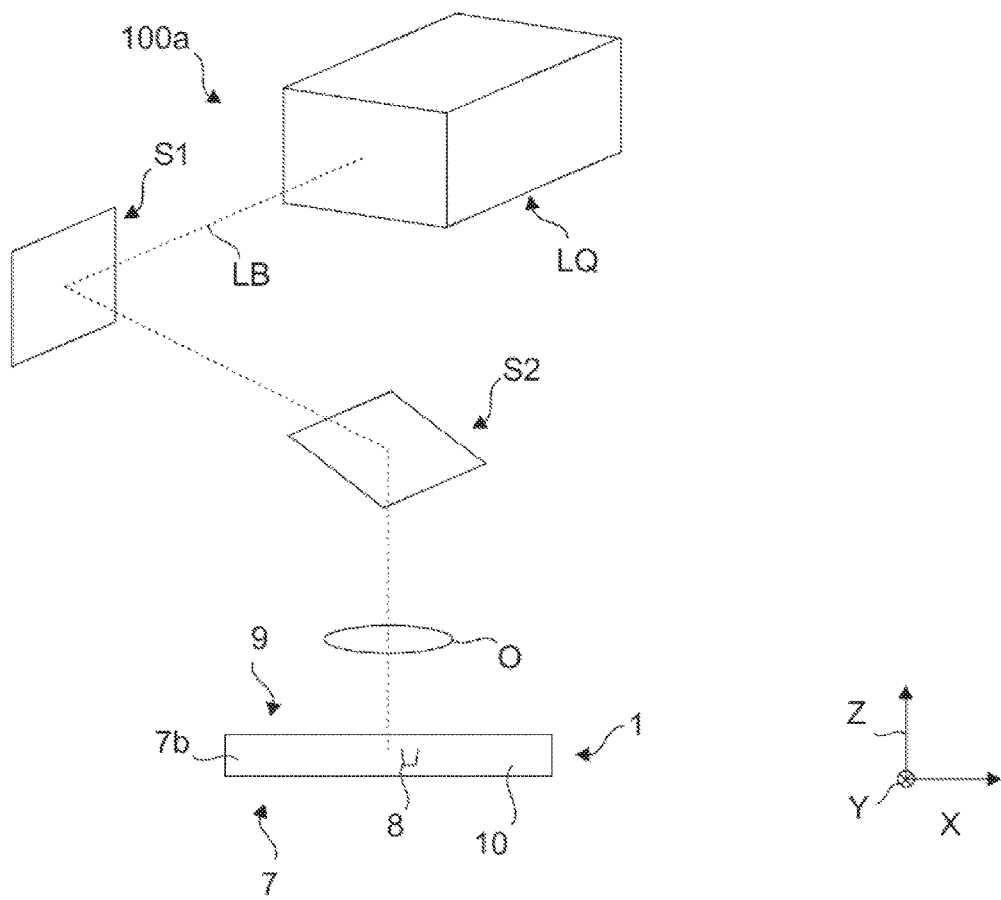
FIG. 4 shows the reference markers being made in a sampling apparatus by means of laser inner engraving.

FIG. 4 shows the basic structure of the method 100a for making reference markers 8 in a sampling apparatus 1 by means of laser inner engraving. The coordinate system shown having the axes x, y, z only apply to the sampling apparatus 1 in this case. Starting from a laser source LQ, a laser beam LB is deflected on two axes using two mirrors S1, S2 by means of a scanner and is focussed into the interior 7b of the body 10 using a lens or an objective lens O, and produces a visible point in the material 9, as described above. By providing many points, the reference markers 8 are produced in the material, and therefore a sampling apparatus 1 according to the invention as described in accordance with FIG. 1-3 is obtained.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Headings are used herein for convenience only.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. In the disclosure and the claims, "and/or" means additionally or alternatively. Moreover, any use of a term in the singular also encompasses plural forms.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

LIST OF REFERENCE SIGNS 1 sampling apparatus
1a longitudinal axis
1b width axis
2 cavity
3 sample
4 measuring region
5 focus region
6 measuring device
7 material region
7a surface region
7b inner region
8 reference marker
9 material
10 body
20 light source
20' light beams
23 lens
88 row
100a method
α, β angle
D top surface
d1, d2 diameter
h height
K1 longitudinal axis
LB laser beam
LQ laser source
M generated surface
ML surface line
O objective lens
x, y, z coordinates

The invention claimed is:

1. A sampling apparatus made of a material, comprising a body of the material forming a cavity for receiving a liquid sample, and comprising a gauging region able to be arranged in a focus region of a visual measuring device for determining the position of the sampling apparatus, the cavity, or both, and in which at least one reference marker is arranged to be detected by means of the visual measuring device, wherein the reference marker is formed in an inner region of the body that is remote from a surface of the body and is in the form of a generated surface and a top surface of a truncated cone.

2. The sampling apparatus according to claim 1, wherein the at least one reference marker is a conversion product of the material.

3. The sampling apparatus according to claim 1, wherein the at least one reference marker is formed by means of laser inner engraving.

4. The sampling apparatus according to claim 1, wherein an angle between a surface line of the truncated cone and a longitudinal axis of the truncated cone has a value within a range of 5–20°.

5. The sampling apparatus according to claim 1 wherein a diameter of the top surface has a value within a range of 1-5 μm.

6. The sampling apparatus according to claim 1 comprising at least two reference markers wherein the reference markers are arranged relative to one another at a distance of 100-1000 μm.

7. The sampling apparatus according to claim 1, wherein one to ten rows of reference markers are arranged along a longitudinal axis of the sampling apparatus and one to ten rows of reference markers are arranged along a width axis of the sampling apparatus.

8. The sampling apparatus according to claim 1, wherein the material of the sampling apparatus is PMMA (polymethyl methacrylate).

9. The sampling apparatus according to claim 1, wherein an angle between a surface line of the truncated cone and a longitudinal axis of the truncated cone has a value of approximately 10°.

10. The sampling apparatus according to claim 1, wherein a diameter of the top surface has a value within a range of approximately 3.2 μm.

11. The sampling apparatus according to claim 1, wherein a diameter of a bottom surface of the truncated cone that is parallel to the top surface has a value within a range of 1-10 μm.

12. The sampling apparatus according to claim 1, wherein a diameter of a bottom surface of the truncated cone that is parallel to the top surface has a value within a range of approximately 5 μm.

13. The sampling apparatus according to claim 1, comprising at least two reference markers wherein the reference markers are arranged relative to one another at a distance of 200-500 μm.

14. The sampling apparatus according to claim 1, comprising at least two reference markers wherein the reference markers are arranged relative to one another at a distance of approximately 250 μm.

15. The sampling apparatus according to claim 1, wherein three rows of reference markers are arranged along a longitudinal axis of the sampling apparatus and three additional rows of reference markers are arranged along a width axis of the sampling apparatus.

16. The sampling apparatus according to claim 1, wherein the material is plastic material, glass, or a combination thereof.

17. A method for making at least one reference marker in a sampling apparatus made of a material, said apparatus comprising a body of the material forming a cavity for receiving a liquid sample, and the sampling apparatus comprising a gauging region arranged in a focus region of a visual measuring device, wherein the reference marker, which is able to be detected by means of the visual measuring device, is in the form of a generated surface and a top surface of a truncated cone and is made in an inner region of the body that is remote from a surface of the body, within the gauging region, by means of laser inner engraving.

18. The method according to claim 17, wherein the material is plastic material, glass, or a combination thereof.

\* \* \* \* \*